United States Patent [19]
Magnussen, Jr. et al.

[11] Patent Number: 5,148,239
[45] Date of Patent: Sep. 15, 1992

[54] HIGH PERFORMANCE ABSORBANCE DETECTOR WITH FLASHLAMP AND COMPACT FOLDED OPTICS SYSTEM

[75] Inventors: Haakon T. Magnussen, Jr., Orinda; Roy P. Moeller, Hayward, both of Calif.

[73] Assignee: Rainin Instrument Co., Inc., Emeryville, Calif.

[21] Appl. No.: 554,247

[22] Filed: Jul. 17, 1990

[51] Int. Cl.$^5$ .......................... G01N 21/27; G01J 3/42
[52] U.S. Cl. .................................. 356/435; 356/319
[58] Field of Search ............... 356/435, 434, 325, 319, 356/334, 409, 319

[56] References Cited

U.S. PATENT DOCUMENTS

| | | | |
|---|---|---|---|
| 3,985,441 | 10/1976 | Schoeffel et al. | 356/325 |
| 4,545,680 | 10/1985 | Smith, Jr. | 356/319 |
| 4,565,447 | 1/1986 | Nelson | 356/319 |
| 4,822,168 | 4/1989 | Nogami et al. | 356/319 |

OTHER PUBLICATIONS

Oriel Corporation-Optics and Filters, vol. III, 1984, p. 82.

*Primary Examiner*—Vincent P. McGraw
*Assistant Examiner*—La Charles P. Keesee, II
*Attorney, Agent, or Firm*—Robert R. Meads

[57] ABSTRACT

A compact high performance absorbance detector including a flashlamp light source and folded optics system with ruled grating reflecting beam splitter for minimizing flash to flash angular pattern and spectral variations of the flashlamp.

15 Claims, 6 Drawing Sheets

HIGH PERFORMANCE ABSORBANCE DETECTOR WITH FLASHLAMP AND COMPACT FOLDED OPTICS SYSTEM

BACKGROUND

The present invention relates to improvements in high performance absorbance detectors and more particularly to such an improved detector including a flashlamp and a compact folded optics system.

U.S. Pat. Nos. 3,810,696 and 4,565,447 describe light absorbance detectors including flashlamps as a pulsed source of light. The Model 490 Multiwavelength HPLC Detector of the Waters Chromatography Division of the Millipore Corporation, Milford, Mass. is a commercial embodiment of the detector described in the '447 patent.

While there are well recognized advantages associated with the use of flashlamps in absorbance detectors relative to power requirements, lamp life, system warm up time and breath of light spectrum, there are also well recognized limitations particularly when it is desired to reduce the noise in such systems to the theoretical shot noise level. In particular, it is recognized that the noise generated in absorbance detectors including flashlamps such as the Waters Model 490 is significantly greater than similar detectors including deuterium lamps and several times greater than the theoretical shot noise level. The flashlamp is the principal source of such greater levels of noise.

In developing the soon to be released, improved performance absorbance detector, the DYNAMAX MODEL UV-1 of the Rainin Instrument Co., Inc., the inventors of the subject matter set forth in this application isolated five primary characteristics of flashlamps which contribute to absorbance noise in high sensitivity absorbance detectors. They are:

(1) light amplitude variations flash to flash,
(2) flashlamp arc position variations from flash to flash,
(3) spatial intensity variations across the surface of the flashlamp arc from flash to flash,
(4) angular light pattern variations from flash to flash, and
(5) light spectrum variations from flash to flash.

In the DYNAMAX MODEL UV-1, each of the foregoing noise characteristics is minimized to produce an absorbance detector having a noise specification of less than $2 \times 10^{-5}$ AU. The first of the above-listed noise characteristics may be compensated for by improved electronics while optics with low spatial sensitivity and improved flow cell design may minimize the effects of the second and third noise characteristics. In accordance with the present invention, noise associated with the third, fourth and fifth noise characteristics are substantially eliminated by the inclusion of a unique reflecting beam splitter with highly polished mirror surfaces and splitter and flow cell masks in the optics system of the DYNAMAX MODEL UV-1.

As to angular pattern variations in consecutive flashes from a flashlamp, since the flashlamp arc is not totally transparent and has spatial variations in its brightness, the normalized radiation intensity in different directions will vary from flash to flash. The relative intensity variations in two different directions is approximately proportional to the angular separation between the two directions for small angles. The typical amplitude of the angular noise is such that two beams separated by an angle of 0.3 degrees results in a filtered absorbance noise of approximately $1.0 \times 10^{-5}$ AU peak-to-peak for a one second rise time and a 3 degree separation results in a filtered absorbance noise of approximately $10 \times 10^{-5}$ AU peak-to-peak.

As to flash to flash spectral variations, the relative intensity of the light as a function of wavelength varies slightly from flash to flash. This has the effect of varying the center wavelength and the spectral shape of the bandpass of the monochromator output of the absorbance detector especially at monitored wavelengths where the light intensity changes rapidly as a function of wavelength. That is, on the sides or shoulders of a spectral peak.

The Waters Model 490 Absorbance Detector virtually eliminates noise due to angular flash pattern variations from the flashlamp source but is severely affected by spectral variations flash to flash. In these regards, the Waters Model 490 and the absorbance detector described in the '447 patent include a beam splitter which intercepts a single beam of light with a semitransparent material that reflects a portion of the beam in one direction and transmits another portion in a different direction. Such beam splitters are commonly made of quartz which reflects on the order of 10% of the incident light and transmits the rest. For quartz coated with a material such as inconel which reflects a greater percentage of light the result may be two beams of similar intensities. Such beam splitters are available from many sources such as the Oriel Corporation of Stratford, Conn.and are described in its catalog entitled "Optics & Filters". In the Waters Model 490, the two resulting beams from such a splitter view the light source essentially in the same direction. Viewing the source from essentially the same direction virtually eliminates noise due to angular light pattern variations from the flashlamp source. Unfortunately however, this type of beam splitter is wavelength sensitive. In particular, the ratio of the intensities of the two resulting beams, the "split ratio", varies as a function of wavelength. The wavelength sensitivity of the split ratio when combined with the flash to flash spectrum variations from the flashlamp causes noise which at many wavelengths over the detected spectrum of wavelengths is considerably larger than the shot noise level.

Accordingly, there are continuing needs for an absorbance detector with flashlamp source and high light throughput which is characterized by a low noise level approaching that of shot noise and which is unaffected by angular pattern and spectral variations flash to flash. The present invention satisfies such needs.

SUMMARY OF INVENTION

In developing the DYMAMAX MODEL UV-1, the inventors discovered an optics system which is substantially unaffected by angular and spectral variations of a flashlamp included in the absorbance detector. The optics system includes a reflecting beam splitter comprising a plurality of sets of small mirrors interspersed as a series of mirrors facing incident light from a light source in the optics system. The mirrors of each set extend at different common angles relative to the incident light such that each set of mirrors develops a different reflected beam, one of which comprises a sample beam and another of which comprises a reference beam for the detector. Each mirror has a width of greater that 0.15 mm and the splitter is positioned relative to the source such that each mirror has a viewing angle of the source which differs from that of its adjacent mirrors by 1 degree or less.

DETAILED DESCRIPTION OF PREFERRED EMBODIMENT OF INVENTION

Figure 1A:
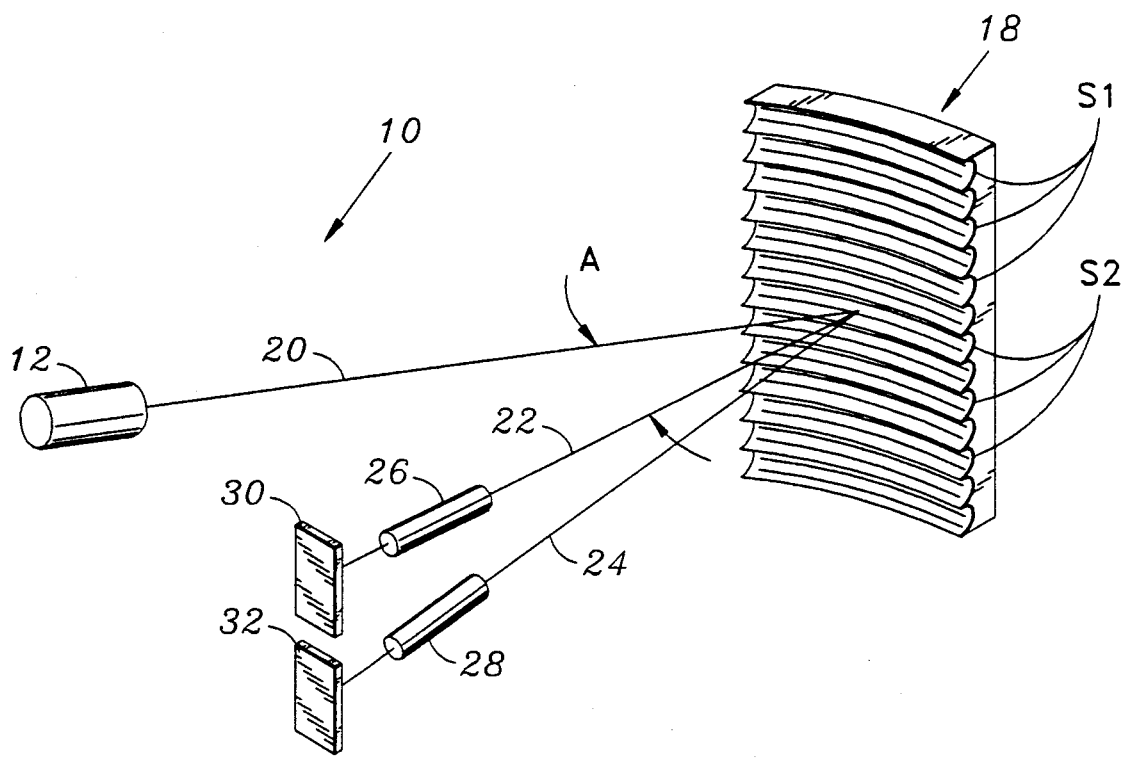
FIG. 1a is a schematic central ray diagram for a simplified version of the optic system of the present invention including a splitter having a series of concave mirrors and functioning as a combined beam splitter and beam focusing element to direct sample and reference beams through sample and reference flow cells in the optic system.
Figure 1B:
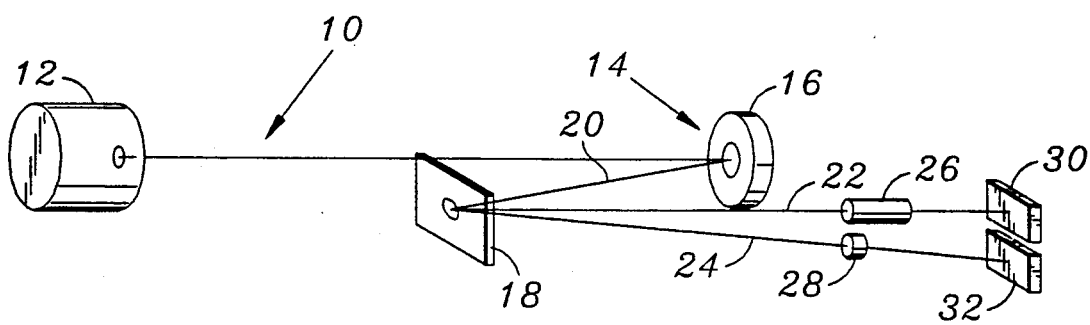
FIG. 1b is a schematic central ray diagram for a simplified version of the optic system of the present invention including a grating reflecting beam splitter comprising a series of flat mirrors and a separate mirror for directing sample and reference beams through sample and reference flow cells in the optic system.

Generally speaking and with reference to the simplified versions of the absorbance detector of the present invention illustrated in FIGS. 1a and 1b, the detector is represented by the number 10 and comprises a flashlamp light source 12 such as a Xe flash lamp, and an optics system 14.

In FIG. 1a the optic system 14 includes a beam splitter 18 for receiving incident light 20 as a series of light flashes from the source 12 and for focusing and reflecting the incident light as sample and reference beams 22 and 24 through sample and reference flow cells 26 and 28 to photo detectors 30 and 32 respectively.

Generally speaking, the splitter 18 included in the optics systems of the present invention may comprise a cube-corner or a grating type of splitter having a plurality of sets of small mirrors interspersed as a series of mirrors facing an incident light beam from a light source in the optics system. The mirrors of each set extend at different common angles relative to the incident light beam such that each set of mirrors develops a different reflected beam, one of which comprises a sample beam and another of which comprises a reference beam for the detector. Each mirror has a width of greater than 0.15 mm and the splitter is positioned relative to the source such that each mirror has a viewing angle of the source which differs from that of its adjacent mirrors by 1 degree of less.

In FIG. 1a, the splitter comprises a series of concave mirrors formed by sets of mirrors S1 and S2. Preferably, the angle A between a source-splitter axis and splitter-cell axis is relatively small so as to allow the use of spherical surfaces for the facets of the mirrors comprising the splitter. That is, the surface of a conic of revolution (SCR) defines the shape of the facet. The surface of a SCR has in general two foci, points in space associated with it, that corresponds to the small object and image positions of a reflector having such a surface. Each facet of each mirror in each set is an individual focusing mirror producing an image of the object which overlaps other images of the same set to form one composite image. The number of sets of mirrors determines the number of reflected beams and composite images (e.g. S1 and S2 define beams 22 and 24 respectively).

In FIG. 1b, the splitter comprises a special geometry where the mirrors are flat. A flat surface can be thought of as a SCR with its foci at infinity thus having no intrinsic focusing power. Thus in FIG. 1b, the optics system includes a concave mirror 16 for receiving a series of light flashes from the source 12 and for reflecting the flashes to a beam splitter 18. For high f-number systems and for beam splitters with small mirror surface angles, the light appears to the splitter to be substantially collimated light. In this regard, and as represented in FIGS. 2a and b, the beam splitter 18 of FIG. 1b may comprise a series of highly polished small flat mirrors having (1) a symmetrical profile, (2) a width of 0.15 mm or greater, (3) a reflected beam angle of 10 degrees or less and (4) a viewing angle of 1 degree or less as defined by the line spacing, the distance between the flashlamp source and the concave mirror 16, the distance between the concave mirror and the beam splitter mirrored surface and the focal length (f) of the concave mirror.

Figure 2A:
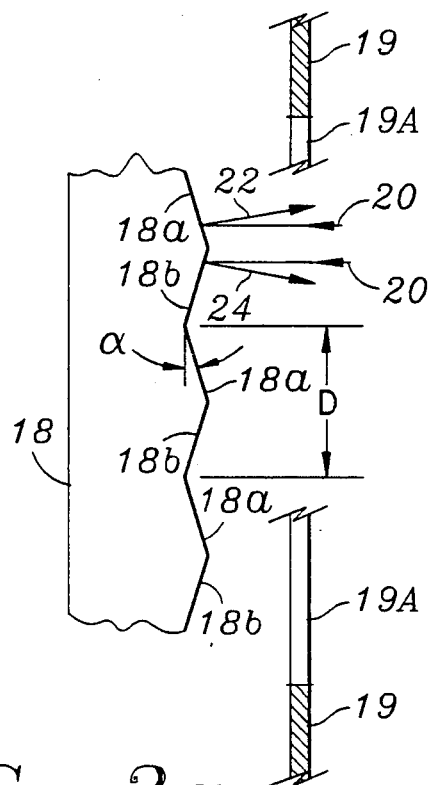
FIG. 2a is a fragmentary side view of a portion of a splitter mask and a beam splitter such as that included in the system of FIG. 1b for developing two reflected beams.

More particularly, the mirror surfaces of the splitter 18 illustrated in FIG. 2a comprises two sets of mirror defining a triangular symmetrical profile. The mirror surfaces are arranged such that one set of mirrors 18a reflects incident light 20 as a reflected beam 22 (sample beam) in one direction. The mirrors 18a are evenly interspersed with a second set of mirrors 18b which reflects incident light as an equivalent reflected beam 24 (reference beam) in a second direction.

Figure 2B:
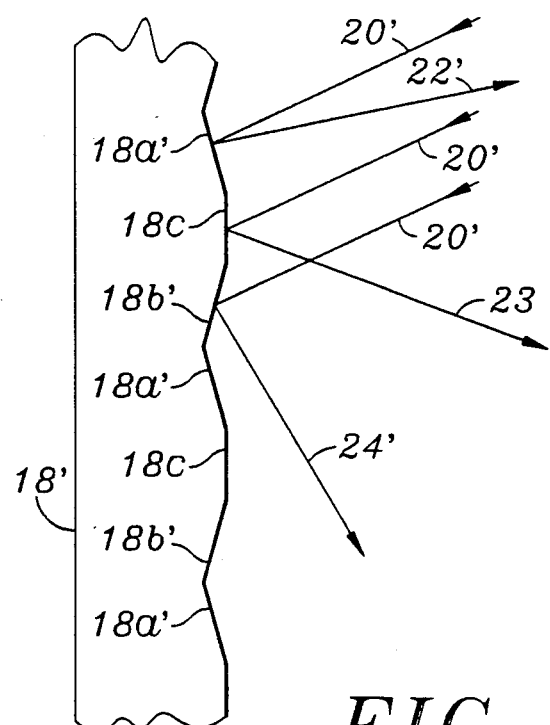
FIG. 2b is a fragmentary side view of a beam splitter for developing three reflected beams for the optic system of the present invention.

The mirror surfaces of the splitter 18' illustrated in FIG. 2b comprise three sets of mirrors defining a symmetrical profile. The mirror surfaces are arranged such that a first set of mirrors 18a' reflects incident light 20' as a first reflected beam 22', a second set of mirrors 18b' evenly interspersed with the mirrors 18a' reflects incident light 20' as a second reflected beam 24' and a third set of mirrors 18c evenly disposed between the mirrors 18a' and 18b' reflects incident light 20' as a third reflected beam 23. Depending upon the specific application for the beam splitter, one or as many as all of the beams formed by such a splitter may be attenuated by an adsorbing media with cells 26 and 28. Further, while the mirror surfaces 18a', 18b' and 18c illustrated in FIG. 2b are evenly spaced and define a series of truncated triangular surfaces, a principal feature of the preferred splitters of the present invention is that the utilized area on the splitter for each beam, e.g. sample and reference, has a common centroid, i.e. common coordinates of centroid, where the coordinates of a centroid in a XY system are represented by $X_c = M_y/A$ and $Y_c = M_x/A$, where $$M_x = \int_A \int y\, dA, \; M_y = \int_A \int x\, dA, \; A = \int_A \int dA$$

and $dA = dxdy$. Having such a common centroid of the utilized area of the splitter has been found to substantially reduce the effects of first order intensity variations across the splitter on the split ratio of the splitter, that is the ratio of the intensity of the reference beam to the sample beam. Also, under such common centroid conditions, the spacing of the mirrors comprising the splitter may vary about the center of the splitter.

Further, since the spacing between the adjacent mirrored surfaces, the beam distance of the source and the splitter from the concave mirror and the f of the concave mirror determine the viewing angle, the spacing between sample and reference flow cells 26 and 28 receiving the reflected beams 22 and 24 or 22' and 24' respectively can be set to any convenient value without effecting the viewing angle. This may be accomplished simply by designing the angle between adjacent mirrored surfaces in the splitter to a required value. It is desirable to keep the angle between the reflected beams to as small an angle as possible which still allows for adequate flow cell separation. As will be described in connection with the optic system of FIG. 3, a small angle of separation equal to or less than 10 degrees allows for a common focusing element, such as a relatively large concave mirror, to be used for the two beams and optical aberrations to be kept to a minimum. In addition, the smaller the angle, the smaller the amount of mirror surface material which must be removed during splitter manufacture and the smoother the resulting mirror surfaces.

For viewing angles of 1 degree or less, it has been found that the resulting differential signal developed by photo detectors 30 and 32 receiving light passing through the sample and reference flow cells 26 and 28 respectively and resulting from angular variations from the source 12 can be reduced to a value less than the shot noise.

Preferably, the spacing D shown in FIG. 2a is 3 or less lines per millimeter with that designed into the DYNAMAX MODEL UV-1 being about 1 line or groove per millimeter. Also, the angle "a" of the mirrored surfaces as shown in FIG. 2a is preferably about 1 to 2 degrees with that designed into the DYNAMAX MODEL UV-1 being about 1.225 degrees plus or minus 0.025 degrees. Further, by way of example if the concave mirror 16 with a focal length of 100 mm is placed at its focal distance of 100 millimeters from the source 12 and the spacing D is 1.0 mm, then the viewing angle of the light source between the reflected beams 22 and 24 is less than 0.3 degrees. While a 100 mm spacing between the source and the concave mirror 16 allows for a very compact optic design, obviously the distance can be different. Making it larger allows for a larger spacing between the mirrored surfaces of the splitter while remaining within the 1 degree or less viewing angle limit and allows for longer focal lengths both of which tend to reduce optical distortions and aberrations at the expense of increased size.

Beam splitters of the general type described hereinabove with respect to FIG. 2a but with large reflected beam angles of 30 to 60 degrees and line spacing of 4 lines per millimeter have been used in the past for general beam splitting applications but have not been used or recommended for image quality splitting applications as is required in a high performance low noise absorbance detector. For example, the course grating beam splitter of the Oriel Corporation includes a equal spacing of 4 lines per millimeter and reflected beam angles of 30, 45 and 60 degrees. As stated in the previously referenced Oriel catalog, since such gratings are not diffraction limited they are not recommended for imaging systems. As previously discussed, with the modifications and limitations discovered by the inventors herein, such modified ruled grating reflecting beam splitters provide means for reducing the effect of the angular radiation variations associated with flashlamp sources.

Further, the preferred grating reflecting beam splitter included in the optic systems of the present invention additionally reduces the effects of the spectral variations noise characteristic of flashlamp sources. As previously discussed, such spectral variations are a principal source of noise in the Waters Model 490 absorbance detector. In fact, anything in an optic design which causes a spectral imbalance between the two beams when combined with the spectral variations from a flashlamp source will cause a differential noise signal resulting in an absorbance noise which may exceed the shot noise level. On the other hand, the preferred grating reflecting beam splitter included in the optics of the present invention has essentially identical spectral characteristics for the sample and reference reflected beams 22 and 24 (or 22' and 24') because each beam is reflected from the same type of surface. By providing identical spectral characteristics for each beam, the beam splitters 18 and 18' avoid the generation of differential noise signals characteristic of the Waters Model 490 detector and represent a significant advance thereover.

More particularly, adjacent angled mirror surfaces 18a and 18b of the splitter 18 and 18a', 18b' and 18c of the splitter 18' are smooth and highly polished. As a result, optical distortion, diffraction and abberations caused by discontinuities, cutter tool marks and uneven surfaces are reduced to a minimum.

As previously mentioned, By satisfying the common centroid condition of the preferred form of the present invention, the ratio of the intensity in the reference and sample beams (i.e. the split ratio R/S) will remain uniform with changes in the intensity of the incident beam with angular pattern variations in the incident beam flash to flash at the source 12. To insure such uniformity of the split ratio for light over the entire surface of the splitter, the optic system 14 may include a splitter mask 19 as shown in FIG. 2a having a central aperture 19A. The splitter mask 19 insures that any irregularities in the edges of the splitter do not produce variations in the split ratio. By constructing the mask with an aperture smaller than the dimensions of the splitter and positioning the mask so that the areas exposed on the splitter satisfy the common centroid condition, the ratio of light flux in the sample beam to that in the reference beam remains unaffected by illuminance variations across the splitter caused by angular variations of the light source. It can be shown that while meeting the centroid condition will eliminate the ratio fluctuations when the splitter surfaces have uniform reflectivity, a slightly different mask position may be required if the reflectivity is not constant. In such a case, the mask can be constructed in a manner such that its position can be adjusted to a position required by the splitter variations to obtain the smallest ratio variation. Such balance substantially reduces detector response to first order derivative noise, which for small viewing angles dominates over all other orders.

Figure 3:
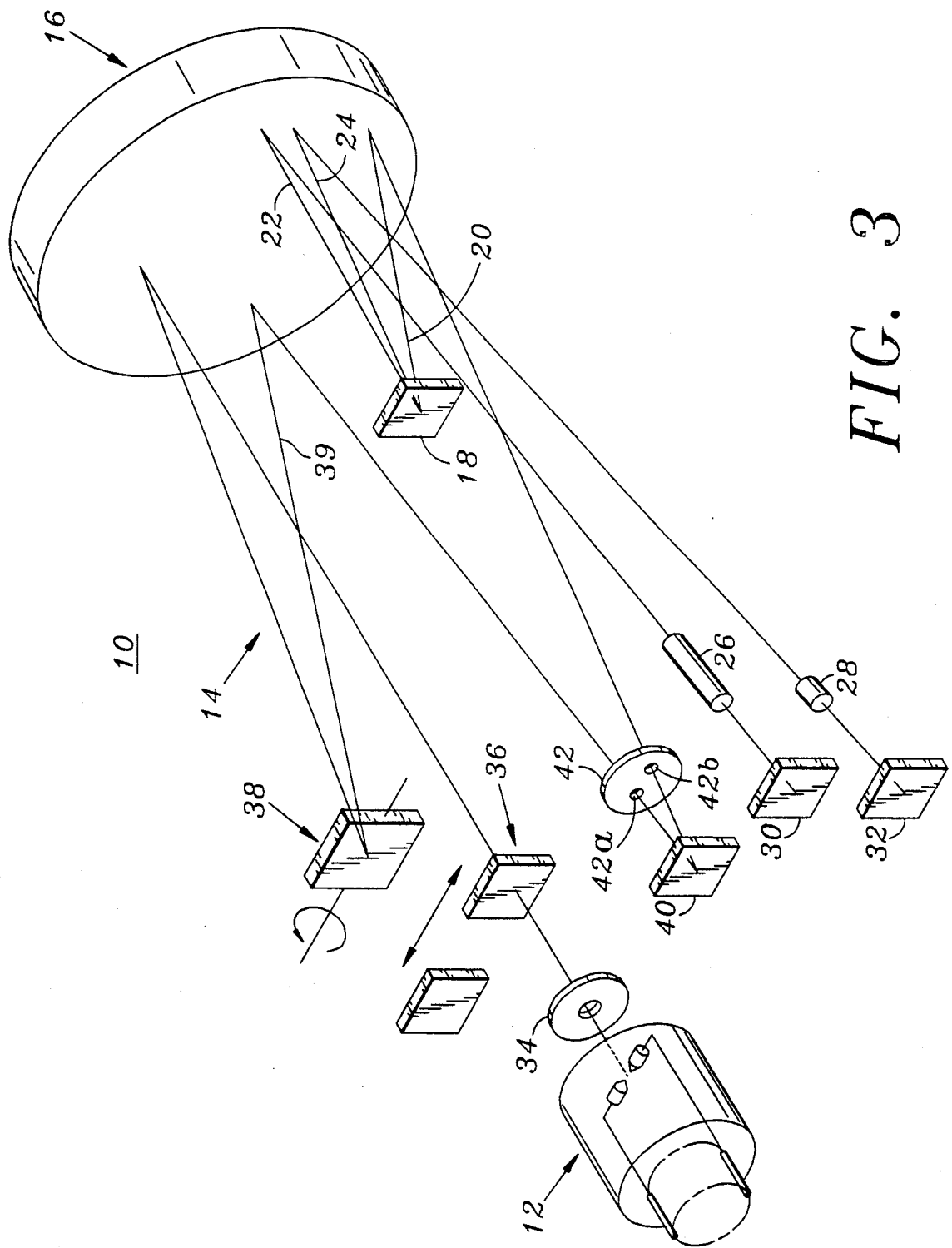
FIG. 3 is a schematic central ray diagram of the folded optics system included in the DYNAMAX MODEL UV-1.

As previously indicated, FIG. 3 depicts the compact folded optics system included in the DYNAMAX MODEL UV-1 absorbance detector. The detector 10 includes the flashlamp source 12, folded optics system 14, relatively large concave mirror 16, beam splitter 18, sample and reference flow cells 26 and 28 and photo detectors 30 and 32 as previously described in general terms in connection with FIGS. 1a, 1b, 2a and 2b. In addition to the foregoing, the detector of FIG. 3 includes a mask 34 for the flashlamp source 12 and a conventional order filter 36. Between the source 12 and the concave mirror 16 is a conventional light diffraction grating 38 for receiving the light flashes reflected from the mirror 16 and for returning to the mirror a light beam 39 centered in wavelength around a wavelength corresponding to the angular position of the grating. Positioned to receive the light beam 39 reflected from the mirror is a front surface relatively small planar mirror 40 separated from the mirror 16 by a mask 42 having entrance iris 42a and exit aperture 42b for passing and returning light from and to the mirror 16.

The light beam reflected from the mirror 16 is substantially collimated light which strikes the mirrored surfaces of the beam splitter 18 to produce sample and reference light beams 22 and 24 for return to and reflection by the mirror 16 to and through the sample and reference flow cells 26 and 28 to the photo detectors 30 and 32. The characteristics of the beam splitter 18 are as previously described for FIG. 1b and significantly reduce the noise producing flash to flash angular pattern and spectral variations in the detector 10. In addition, a mask 19 may be included in the optics system 14 of FIG. 3 with the same benefits as previously discussed. Also, a mask 25 may be included for each of the sample and reference flow cells 26 and 28 as illustrated in FIG. 5b.

Figure 5A:
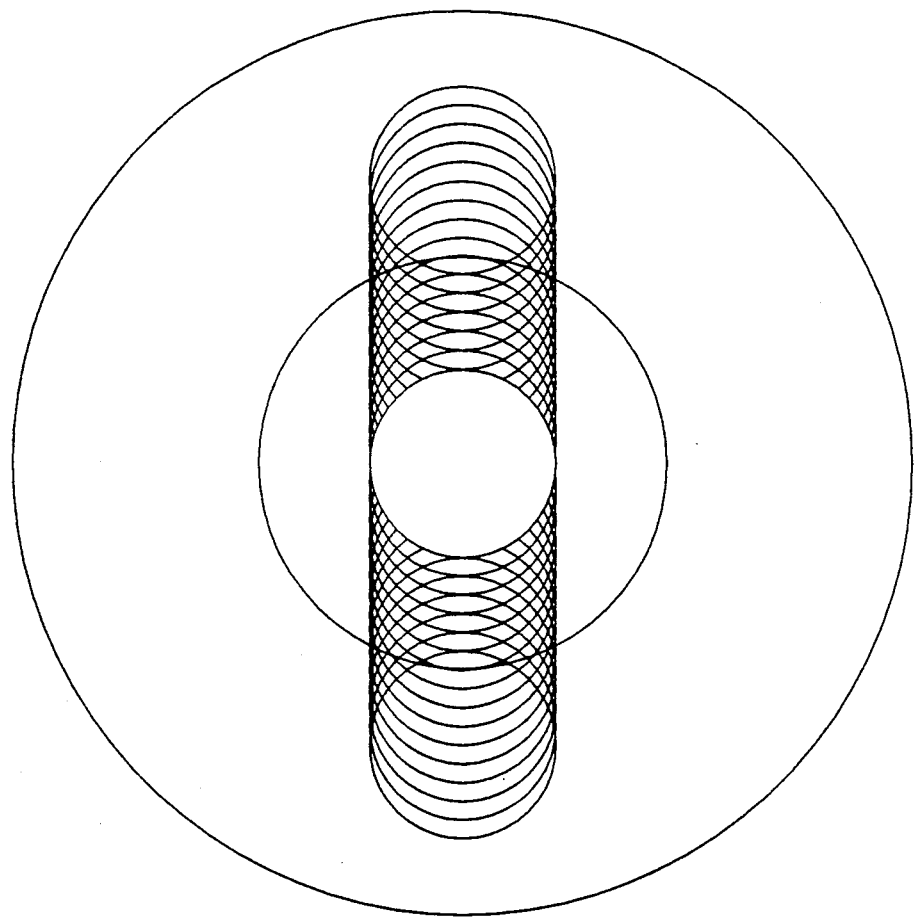
FIG. 5a illustrates a image of the folded optics exit aperture on a sample flow cell thereof with a series of diffracted images above and below a central or main image.
Figure 5B:
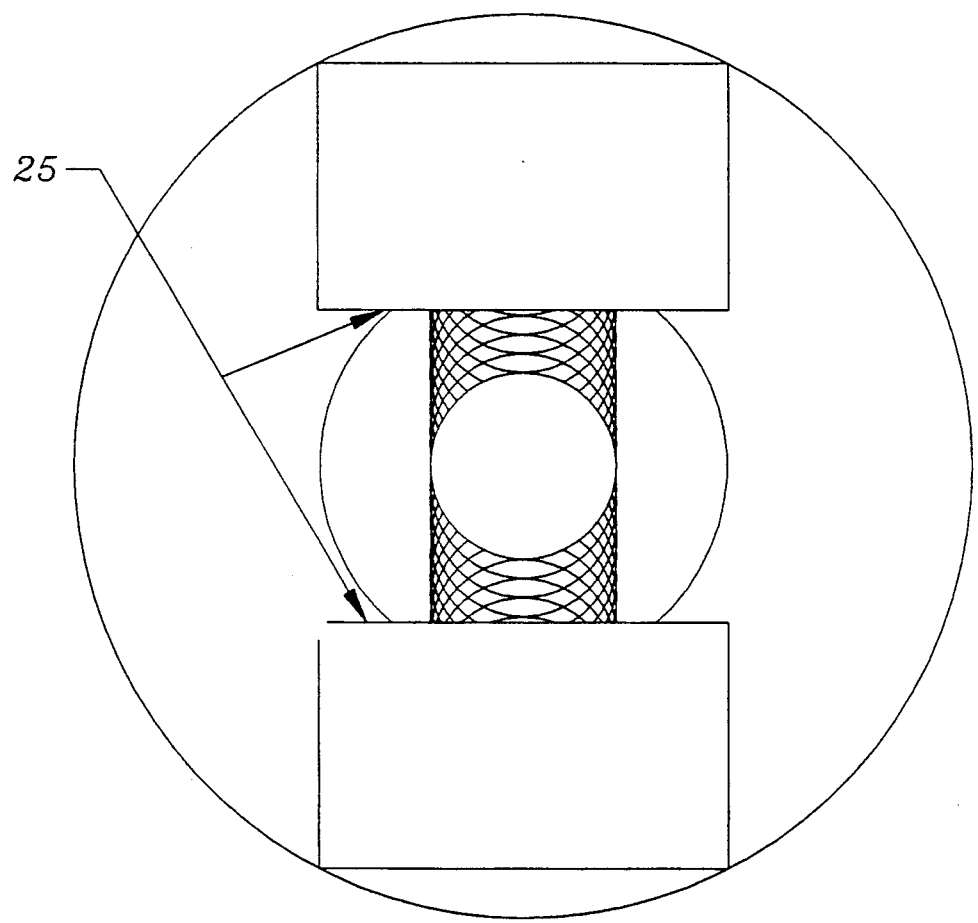
FIG. 5b illustrates a mask over the flow cell entry port in FIG. 5a to eliminate spatial noise from occurring when the main image is shifted in a direction perpendicular to the direction in which the images are diffracted.

More particularly, FIG. 5a illustrates an image of the exit aperture 42b centered on the sample or reference flow cell. Also, illustrated is a series of many diffracted images above and below the central or main image. The diffracted images are due to the fact that the beam splitter is made up of a series of repeating mirrored surfaces which cause diffraction to the incident beam. From the classical grating diffraction equation it can be determined that the spacing between each order at the flow cell is approximately 0.001 inches when the spacing between the splitter groves in 1 mm, the wavelength is 254 nm, and the equivalent distance between the splitter and focal point in the flow cell is 100 mm.

The central or main image (zero order) typically contains over 90% of the total light flux. Because of spatial noise on the images it is important that the sample and reference beams be treated equally in the flow cell especially with respect to the main image. If the light passing through the sample flow cell is clipped differently than the light passing through the reference flow cell then the beams become imbalanced with respect to spatial noise and excess noise will result. The magnitude of such excess noise depends on the severity of the imbalance.

Ideally, all light in each beam should clear each flow cell passage so that none is lost, except to absorption, so that no spatial imbalance results. The main image can be made small enough to easily clear a sample cell passage. Unfortunately, the diffracted images extend distances far above and below the main image making it impractical to pass all of the diffracted light through a small flow cell. The diffracted light must be cut off at some point by the dimension of the flow cell as shown if FIGS. 5a and 5b. Cutting the diffracted light differently in the sample and reference cells can create imbalance resulting in excess noise. Fortunately, the intensity of all diffracted images summed together is small compared to the main image which helps reduce the severity of the problem. In addition, the intensity distribution between the various orders of diffracted images varies slowly between the central image and the edge of the flow cell passage. This fact combined with the large number of orders that are image between the center and edge of a flow cell passage tends to average out spatial variations in the vertical direction. The averaging of spatial variations in the vertical direction (direction of diffraction) greatly reduces the sensitivity to spatial imbalance resulting from uneven blocking of the light beam in the vertical direction between the sample and reference flow cells.

The averaging effect in the vertical direction referred to above does not exist in the horizontal direction (at right angles to the diffracted light). Spatial information is preserved in the horizontal dimension, and, therefore, excess noise due to spatial imbalance between the sample and reference flow cell passages is more likely to occur due to misalignment in the horizontal direction than in the vertical direction. When a beam is centered on a flow cell passage, as shown in FIGS. 5a and 5b, spatial characteristics which distinguish between left and right are balanced. If the optic beam is shifted off center in the horizontal direction, that is perpendicular to the direction which the images are diffracted by the splitter, the upper and lower edges of the passage will clip the diffracted images asymmetrically so that a spatial imbalance results. Unless this imbalance is matched in the reference beam excess noise will result.

One of the objectives in the design of a good high performance liquid chromatography (HPLC) absorbance detector is to allow for easy flow cell interchangeability by the user without the need for realignment. Due to small differences in the construction of individual flow cells, changing flow cells in an instrument will produce small changes in the positions of the passages relative to the optic beam. These small changes in position from one flow cell to another may cause the excess noise due to spatial imbalance to become larger than desired in an flow cell which was not used to align the optics system. To reduce the sensitivity of spatial imbalance to flow cell positioning it is first assumed that the main image completely clears both flow cell passages with no clipping so that we are only concerned with diffracted images. Then a simple approach to reducing spatial imbalance sensitivity to flow cell position changes is to place a mask 25 having a horizontally elongated slit 25A in front of each flow cell passage, that is a slot elongated in a direction substantially normal to the direction in which the images are diffracted by the splitter. The mask 25 clips the beam on a line at a right angle to the diffracted light as shown in FIG. 5b. The slit mask effectively eliminates spacial balance changes from occurring when the image is shifted in a horizontal direction, along the direction of the slit, until the beam touches a side of the passageway. If the slit mask is not placed at the focal point of the images then its optimum shape may not be a rectangular slit with straight parallel side as illustrated. Rather, a dumbbell-shaped slit with curved sides and a slit width narrowest in the center and widening to each side may be desired if the slit mask is placed somewhere in front of the focal point.

Figure 4:
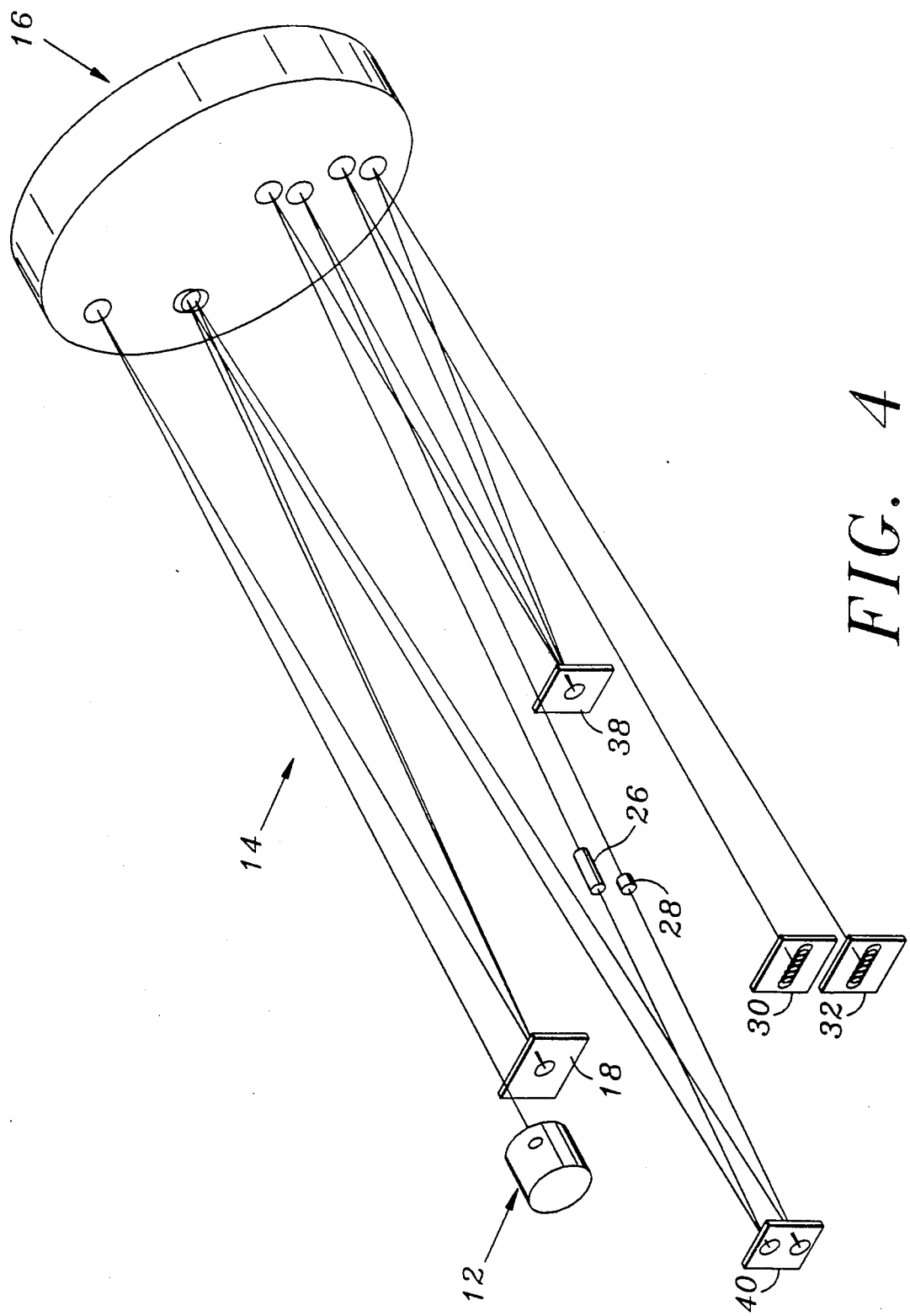
FIG. 4 is a schematic central ray diagram (not to scale) of an optics system for an array detector in accordance with the present invention.

A ray diagram, not to scale, and similar to that of FIG. 3, but for an array detector, is illustrated in FIG. 4. As shown, the optics of the array detector is nearly identical to that of the DYNAMAX MODEL UV-1 of FIG. 3 except that the positions of the grating 38 and beam splitter 18 are reversed and the position of the flow cells has changed. Also, the splitter mask 19 and the flow cell masks 25 may be included in the optics system 14 of FIG. 4 with the benefits previously described.

As shown, in the array detector of FIG. 4, light reflected from the front surface mirror 40 passes through the sample and reference flow cells 26 and 28, strikes the mirror 16 and is then reflected to the grating 38 for generation of a light beam centered in wavelength about a wavelength controlled by the angular position of the grating. The beam from the grating 38 is reflected by the mirror 16 to photo detectors comprising photo diode arrays.

Again, the characteristics of the beam splitter 18 are as previously described to resolve the noise characteristics of the flashlamp source relative to angular pattern and spectral variations flash to flash.

Further, in the array detector, two (or more) beams of white light generated in collimated light by the splitter 18 are brought to focus at the position of the flow cells after being retro reflected by the front surface mirror 40. The flow cells are one focal length from the concave mirror 16 so that collimated light results when light from the flow cells strikes the concave mirror. The two beams of collimated light begin to merge as they approach the position of the grating 38. For optimum performance, the grating should be placed at the position where the splitter is imaged, that is where the two beams completely overlap forming an image of the splitter. The collimated light is diffracted by the grating and the first order spectrum is directed to the concave mirror 16. The reflected beams then are brought to focus on the pair of photo diode arrays where a sharp image of the spectrum appears. One spectrum represents the light that passes through the sample cell and the other represents the light that passes through the reference cell.

While preferred embodiments of the present invention have been described in detail hereinabove and have been directed to an absorbance detector with a flashlamp, changes and modifications may be made in the embodiments without departing from the scope or spirit of the present invention as defined by the following claims. For example, the splitter and folded optic system described hereinabove may be useful with lamps other than flashlamps.

We claim:

1. A high performance absorbance detector, comprising:
    a light source;
    optic means responsive to incident light from the source and including a reflecting beam splitter comprising a plurality of sets of small mirrors interspersed as a series of mirrors facing incident light from the source, the mirrors of each set extending at different common angles relative to the incident light such that each set of mirrors develops a different reflected beam, one of which comprises a sample beam and another of which comprises a reference beam, each mirror having a width of greater than 0.15 mm and the splitter positioned relative to the source such that each mirror has a viewing angle to the source which differs from that of its adjacent mirrors by 1 degree or less;
    a sample flow cell for passing the sample beam; and
    photo detecting means for separately detecting the sample beam passing through the flow cell and the reference beam.

2. The detector of claim 1 wherein each mirror comprises a concave facet for focusing and reflecting incident light as a reflected beam.

3. The detector of claim 1 wherein each mirror comprises a flat facet and series of mirrors have a symmetrical profile.

4. The detector of claim 1 wherein the mirrors of each set receive incident light over and reflect light from an area having a centroid common with that of the other sets of mirrors.

5. The detector of claim 1 further comprising a splitter mask with an aperture positioned such that the mirrors of each set receive incident light and reflect light from an area having a centroid common with that of the other sets of mirrors.

6. The detector of claim 1 wherein the light source is a flashlamp for generating a series of light flashes and the optic means is responsive to the light flashes.

7. The detector of claim 1 wherein the beam splitter has a reflected beam angle of ten degrees or less.

8. The detector of claim 1 further including masks over entrances to the sample and reference flow cells having slits therein elongated in directions substantially normal to directions in which images are diffracted by the splitter.

9. In a high performance absorbance detector comprising a light source for generating incident light, a beam splitter generating a plurality of reflected light beams, a sample flow cell for passing one of the beams developed by the beam splitter and photo detector means for detecting the beams passing through the flow cell, the improvement comprising:
    a reflecting beam splitter comprising a plurality of sets of small mirrors interspersed as a series of mirrors facing incident light from the source, the mirrors of each set extending at different common angles relative to the incident light such that each set of mirrors develops a different reflected beam, one of which comprises a sample beam and another of which comprises a reference beam, each mirror having a width of greater than 0.15 mm and the splitter positioned relative to the source such that each mirror has a viewing angle to the source which differs from that of its adjacent mirrors by 1 degree of less.

10. A highly compact HPLC variable wavelength absorbance detector, comprising:
    a light source for generating incident light;
    optic means responsive to the incident light including
        a relatively large concave mirror for first receiving the incident light from the source,
        a light diffraction grating between the source and the large concave mirror for receiving the light reflected from the large concave mirror and for returning to the large concave mirror a light beam centered in wavelength around a wavelength corresponding to the angular position of the grating, and
        a relatively small front surface mirror for receiving the light beam reflected once from the large concave mirror and for returning the once reflected light beam to the large concave mirror for a second refletion as a substantially collimated beam of light;

a reflecting beam splitter comprising a plurality of sets of small mirrors interspersed as a series of mirrors facing the substantially callimated light from the large concave mirror, the mirrors of each set extending at different common angles relative to the callimated light such that each set of mirrors develops a different reflected beam, one of which comprises a sample beam and another of which comprises a reference beam, each mirror having a width of greater that 0.15 mm and the splitter positioned relative to the source such that each mirror has a viewing angle of the source which differs from that of its adjacent mirrors by 1 degree or less;

a sample flow cell for passing the sample beam; and photo detector means for separately detecting the sample beam passing through the flow cell and the reference beam.

11. The detector of claim 10 further including a splitter mask with a aperture positioned such that the mirrors of each set receive incident light over and reflect light from an area having a centroid common with such areas of other sets of the mirrors.

12. The detector of claim 10 including masks over entrances to the flow cell and having slits therein elongated in directions substantially normal to directions in which images are diffracted by the splitter.

13. The absorbance detector of claim 10 wherein the beam splitter includes a reflected beam angle of ten or less degrees.

14. A compact high performance array detector, comprising:

a light source for generating incident light; and optic means including a relatively large concave mirror for first reflecting the incident light from the source, a reflecting beam splitter comprising a plurality of sets of small mirrors interspersed as a series of mirrors facing incident light, the mirrors of each set extending at different common angles relative to the incident light such that each set of mirrors develops a different reflected beam, one of which comprises a sample beam and another of which comprises a reference beam reflected to the large concave mirror, each mirror having a width of greater that 0.15 mm and the splitter positioned relative to the source such that each mirror has a viewing angle of the source which differs from its adjacent mirrors by 1 degree of less;

a front surface mirror for receiving the plurality of beams from the large concave mirror and for reflecting the sample beam through a sample flow cell positioned one focal length from the large concave mirror such that collimated light results when the sample beam from the flow cell strikes the large concave mirror, and a light diffraction grating positioned near an image of the splitter for receiving the collimated light beams from the large concave mirror and for diffracting the beams as a first order spectrum directed to the large concave mirror for focusing thereby on a pair of photodiode array detectors, one spectrum representing the light that passes through the sample flow cell and another spectrum representing the reference beam.

15. The array detector of claim 14 wherein the beam splitter includes a reflected beam angle of ten degrees or less.

* * * * *